United States Patent [19]

Roy

[11] Patent Number: 4,816,403
[45] Date of Patent: Mar. 28, 1989

[54] DETOXIFICATION OF CHLORINATED AROMATIC COMPOUNDS BY ORGANISM NRRL B-18086

[75] Inventor: Dipak Roy, Baton Rouge, La.

[73] Assignee: Louisiana State University, Baton Rouge, La.

[21] Appl. No.: 892,312

[22] Filed: Aug. 4, 1986

[51] Int. Cl.$^4$ .......................... C12N 1/20; C12R 1/38; C02F 3/00

[52] U.S. Cl. .................................. 435/253.3; 435/262; 435/874; 210/611; 210/909

[58] Field of Search ....................... 435/253, 262, 874; 210/909, 611

[56] References Cited

U.S. PATENT DOCUMENTS

| | | | |
|---|---|---|---|
| 4,477,570 | 10/1984 | Colaruotolo et al. | 435/253 |
| 4,535,061 | 8/1985 | Chakrebarty et al. | 435/253 |
| 4,664,805 | 5/1987 | Focht | 210/611 |

OTHER PUBLICATIONS

Sinton et al., (1986) Enzyne Microb. Technol. 8, 395–403.
ATCC Catalogue of Bacteria, Phages, and DNA Vectors 16th Edition 1985, pp. 142–143.

*Primary Examiner*—Blondel Hazel
*Assistant Examiner*—Charles L. Patterson, Jr.
*Attorney, Agent, or Firm*—William David Kiesel; Robert C. Tucker; Timothy J. Monahan

[57] ABSTRACT

Pseudomonas strain NRRL B-18086 was isolated as pure culture from the Baton Rouge Sewage Treatment Plant. The strain can utilize chlorinated aromatic compounds as the sole carbon source and will degrade both 2,4-dichlorophenoxyacetic acid (2,4-D) and 2,4,5-trichlorophenoxyacetic acid (2,4,5-T), as well as other xenobiotic compounds.

3 Claims, No Drawings

DETOXIFICATION OF CHLORINATED AROMATIC COMPOUNDS BY ORGANISM NRRL B-18086

STATEMENT REGARDING FEDERALLY SPONSORED RESEARCH

This invention was made with Government support through a two year grant by the United States Environmental Protection Agency to the Hazardous Waste Research Center of Louisiana State University covering Jan. 1, 1985 to Dec. 31, 1986. The government may have certain rights in this invention.

CROSS REFERENCE

This application is related to co-pending application Ser. No. 892,253 filed on Aug. 4, 1986 entitled Detoxification of Chlorinated Aromatic Compounds by Organism NRRL B-18087.

BACKGROUND OF THE INVENTION

1. Field of the Invention

This invention relates to detoxifying chlorinated aromatic compounds with enzymes produced from microorganisms.

2. Description of the Prior Art

Chlorinated aromatic compounds such as 2,4, Dichlorophenoxyacetic Acid (2,4-D) were synthesized in recent decades out of industrial and agricultural necessity. Unfortunately, these toxic compounds are hazardous when released to the environment. Such releases may be purposeful, as occurs with pest control, or they may be by accident from leakage or improper waste control. Microbes occurring in nature did not have the necessary enzymes to degrade these compounds. However, due to continuous exposure of natural microorganisms to these xenebiotic chemicals, a few groups of microorganisms have developed an enzymatic system which is resistant to toxic compounds and are capable of degrading them at a slow rate.

The evolution of microorganisms with biodegradable capability has occurred due to adaptation and furthermore, mainly from the mutations of extrachromosomal DNA replicons classified as plasmids. Plasmids play an important role in the adaptation of a mixed population to an environmental stress and they are capable of transmittal to intergenetic and intragenetic bacterial species to spread the necessary genetic information.

The occurance of genetic information for catabolic pathways on extrachromosomal plasmid DNA has been known for several years. Also known is the capacity of various strains of Pseudomonas for catabolizing salicylate, camphor, octance and naphthalene all of which have genetic information on their plasmids. (Chakraborty et al, "Genetic Regulation of Octane Dissimilation plasmid in Pseudomonas", Proc. Natl. Acad. Sci., 70, 1137–1140, 1973; Dunn and Gunsalus, "Transmissible Plasmid Coding Early Enzymes of Naphthalene Oxidation in *Pseudomonas putida*", J. Bacteriol., 114: 974–979, 1973; Rheinwald et al, "A transmissible Plasmid Controlling Camphor Oxidation in *Pseudomonas putida*", Proc. Natl. Acad. Sci., 70, 885–889, 1973).

The existence of a plasmid in *Pseudomonas putida* which codes the necessary enzymes for the degradation of three aromatic compounds was known by 1974. The metabolic pathway requires at least two hydroxyl groups prior to the cleavage of the aromatic rings. (Dagley, "Catabolism of Aromatic Compounds by Microorganisms", Adv. Micro. Physiol., 6: 1–46, 1971). However, there is an exception with *Bacillus brevis* which was isolated from the contaminated Mississippi River. This strain has an enzyme which can degrade aromatic hydrocarbons with only one hydroxyl group. (Crawford et al, "Catabolism of 5 Chlorosalicylate by a Bacillus Isolated from The Mississippi River", Applied and Environmental Microbiology, Vol. 38, No. 3, 379–384, September 1979).

Recent research in this country has reported *Pseudomonas cepacia* strains capable of biodegrading halophenals with similar research in Russia and India where two other strains of Pseudomonas capable of biodegrading chlorinated organics have been reported. (Karns et al, "Regulation of 2,4,5 Trichlorophenoxyacetic Acid And Chlorophenol Metabolism In *Pseudomonas cepacia* Ac 1100", Applied and Environmental Microbiology, 46, 5, 1182–1186, November 1983; Karns et al, "Metabolism of Halophenols By 2,4,5 Trichlorophenoxyacetic Acid Degrading *Pseudomonas cepacia*", Applied and Environmental Microbiology, 46, 5, 1176–1181, Novemeber 1983; Golovleva et al, "Degradation of Polychloroaromatic Insecticides by *Pseudomonas aeruginosa* Containing Biodegradation Plasmids", Translated from Mikrobiologiya, 51: No. 6, 973–978, 1982. Arunakumari and Mahadevan, "Utilization of Aromatic Substances by *Pseudomonas solancearum*", Indian Journal of Experimental Biology", 22, 32–36, January 1984). It is normally hypothesized that biodegradation of chlorinated organics may be by the dehalogenase enzymes which are typically found in soil microorganisms. The presence of the dehalogenase enzymes in soil micro-organisms has been observed in 16 isolates. Within these isolates four types of dehalogenase activity were noted. (Hardman and Slater, "Dehalogenases In Soil Bacteria", Jour. of General Microbiology, 123, 117–128, 1981). Pseudomonas have two dehalogenase enzymes, one of which is comparable to enzymes in other soil isolates whereas the second enzyme is unique to Pseudomonas.

Microorganisms in nature have been noted to withstand inorganic toxic pollutants such as heavy metals. The fate and transport of heavy metals in the natural environment have been studied. In particular, *Thiobacillus ferroxidans* has been found to be resistant to high concentrations of heavy metals. (Dissanayake, "Metal-Organic Interactions In Environmental Pollution", Intern. J. Environmental Studies, 22, 25–42, 1983). This was supported by experimental data showing the capability of Thiobacillus species containing plasmids which may encode heavy metal resistance. (Davidson and Summers, "Wide Host Range Plasmid Function In The Genus Thiobacillus", Applied and Environmental Microbiology, 46, 3, 565–572, September 1983.)

Microorganisms present in nature undergo genetic modifications and can cope with many toxic compounds under ideal conditions. (Slater and Bull, "Environmental Microbiology Biodegradation", Phil. Trans. Soc. Lond., B297, 575–579, 1982). However, most of what is known in this area has been performed using pure culture—pure substrate systems and available information of the growth kinetics of those microbes is relatively meager. In both natural and man-made environments, microbes are present in a diversity of substrates and their behavior is distinctly different from that of a pure system. (Harder and Dijrhuizen, "Strategies of Mixed Substrate Utilization in Microorganisms", Phil. Trans. R. Soc. Lond., B297, 459–480, 1982; Williams, "Genetic Interactions Between Mixed Microbial Populations", Phil. Trans. R. Soc. Lond., B297: 631–639, 1982).

Biodegradation of an organic compound which is not necessarily a growth substrate can be accomplished by the process of co-metabolism. Co-metabolism is defined as the transformation of a non-growth substrate in the obligate presence of a growth substrate or another transformable compound. (Dalton and Stirling, "Co-Metabolism", Phil. Trans. R. Soc. Lond., B297, 481–496, 1982). Biodegradation of chlorinated organics as co-metabolites have been observed for Pseudomonas and soil microbes. (Francis et al, "Co-metabolism of DDT Analogs By A Pseudomonas Sp.", Applied and Environmental Microbiology, 35, 2, 364–367, February 1978; Hartman et al, "Metabolism of 3-Chloro-, 4-Chloro-, and 3,5-Dichlorobenzoate By a Pseudomonas", Applied and Environmental Microbiology, 37, 3, 421–428, March 1979; Marinucci and Bartha, "Biodegradation of 1,2,3 and 1,2,4 Trichlorobenzene in Soil and in Liquid Enrichment Culture", Applied and Environmental Microbiology, 38, 5, 811–817, November 1979). Enzymatic conversion of 2,4,5T to 2,4,5 trichlorophenol (TCP) by Pseudomonas where conversion of TCP was repressed by an alternate carbon source has also been observed. (Karns et al, "Metabolism of Halophenols By 2,4,5 Trichlorophenoxyacetic Acid Degrading *Pseudomonas cepacia*", Applied and Environmental Microbiology, 46, 5, 1176–1181, November 1983).

Plasmids in microbes attribute biodegrading properties, but have a form of finite stability. Adaptative and environmental changes result in oscillations in the proportion of plasmid containing microorganisms. (Borisoglebskaya and Boronin, "Population Changes in the *Pseudomonas putida* strain BSA202 carrying plasmid, NPL-1 for Naphthalene Catabolism", Translated from Mikrobiologiya, 52: No. 2, 301–306, 1983; Gorlatova and Golovleva, "Population Dynamics of P-xylene Assimilating *Pseudomonas aeruginosa*", Translated from Mikrobiologiya, 52: No. 3, 392–395, 1983; Helling et al, "The Maintenance of Plasmid Containing Organisms in Populations of *Escherichia coli*", Jour. of General Microbiology, 123, 129–141, 1981; Ollis, "Industrial Fermentations With (Unstable) Recombination Cultures", Phil. Trans. R. Soc. Lond., B297, 617–629, 1982). As the plasmid containing fraction of microorganisms are capable of biodegradation, the oscillation of the active fraction results in an oscillation of the rate of biodegradation. Also, the growth criteria of plasmid active species differ from those of plasmid free species. A survey of the prior art shows that although microbes capable of degrading hazardous organic and inorganic waste have been isolated, little is known regarding the growth kinetics and stability of these microbes in a mixed culture, multiple substrate system. A system which is the most comparable to the real world. Additionally, the prior art lacks information concerning the applicability of using microbial dehalogenase enzyme systems to detoxify chlorinated organic compounds.

SUMMARY OF THE INVENTION

A strain of the micro-organism Pseudomonas NRRL B-18086, has now been found which is capable of producing dehalogenase enzymes which can biodegrade chloroaromatic compounds. An unrestricted deposit of this previously undescribed organism was made with the Agricultural Research Service Culture Collection on July 25, 1986, under Accession No. NRRL B-18086. The deposit has been accepted under the Budapest Treaty. All restrictions on the availability of progeny of the strain to the public will be irrevocably removed upon the granting of a patent of which the strain is a subject.

DETAILED DESCRIPTION

Through the process of selective enrichment, two new Pseudomonas bacteria capable of biodegrading chloroaromatic compounds have been isolated from the mixed microbial culture obtained from the Baton Rouge Sewage Treatment Plant. One of these bacteria isolates is the subject of the co-pending application Ser. No. 892,253 entitled Detoxification of Chlorinated Aromatic Compounds by Organism NRRL B-18087. The second bacteria isolate is the subject of this application. Routine biochemical test were performed to determine the taxonomic classification of these isolates. The results of these tests for NRRL B-18086 are shown on Table 1 below. Based on these properties, a profile comparison was made with those included in the rapid NFT data base of DMS Laboratories, Inc., Plainview, N.Y. NRRL B-18086 was identifiable at the genus level to be Pseudomonas. This was further verified by independent testing conducted by API Analytab Products, Plainview, N.Y.

TABLE 1

| Characteristics of Pseudomonas Isolates NRRL B-18086 | |
|---|---|
| Test | Pseudomonas Isolate NRRL B-18086 |
| 1. Gram Stain | -ve |
| 2. Shape | Rods |
| 3. Flagella | Polar |
| 4. Motility | + |
| 5. Pigment | White-Yellow Tint |
| 6. G + C % | 50.1 |
| 7. Growth | |
| 30° | + |
| 35° | + |
| 25° | + |
| 42° | − |
| 8. Oxidase | + |
| 9. Catalase | + |
| 10. Fermentor | − |
| 11. Glucose Oxidizer | + |
| 12. Growth | |
| Blood Agar | + large colony |
| Nutrient Agar | + |
| MacConkey Agar | + |
| Peptone-Yeast Ex. | + |
| Peptone-Agar (Ps. Agar) | + |
| Cetrimide | + yellow colony |
| 13. TSI | No change |
| 14. H$_2$S | + |
| 15. Nitrate Reduction | + |
| 16. Nitrite Reduction | + |
| 17. Tryptophanase | − |
| 18. Arginine Dehydrolase | + |
| 19. Lysine Decarboxylase | − |
| 20. Urease | − |
| 21. Ornithine Decarboxylase | − |
| 22. Esculin Hydrolysis | − |
| 23. Tryptophan Deaminase | − |
| 24. Gelatinase | − |
| 25. Beta-d-galacto-sidase | − |
| 26. O—nitrophenyl- -d- galactoside | − |
| 27. Arabinose | − |
| 28. Mannose | − |
| 29. Rhamnose | − |
| 30. Saccharose (sucrose) | − |
| 31. Melibiose | − |

TABLE 1-continued

| Characteristics of Pseudomonas Isolates NRRL B-18086 | | |
|---|---|---|
| | Test | Pseudomonas Isolate NRRL B-18086 |
| 32. | Maltose | − |
| 33. | Inositol | − |
| 34. | Sorbitol | − |
| 35. | N—acetyl-glucosamine | − |
| 36. | Gluconate | + |
| 37. | Caprate | + |
| 38. | Adipate | + |
| 39. | Malate | + |
| 40. | Citrate | + |
| 41. | Phenyl Acetate | + |
| 42. | Amygdalin | − |
| 43. | Indole Production | − |
| 44. | Voges-Proskauer Test | + |

Isolates NRRL B-18086 is gram negative, nonfermentative, motile rod. It is white with an approximate size of $3.7 \times 1.3 \mu$ with polar flagella.

The mean guanine plus cytosine (GC) content of the chromosomal DNA of the isolate was obtained from the cesium chloride buoyant density determined by analytical ultracentrifuge. The GC content of the isolate using poly dAT standards was calculated to be 50.1.

The newly isolated strain of Pseudomonas is capable of utilizing chlorinated aromatic compounds as the sole carbon source. The isolate contains dehalogenase activities and the enzyme can be detected by release of Cl− from the 2,4-dichlorophenoxyacetic acid (2,4D), 2,4-dichlorophenol, 2,4,5-trichlorophenoxyacetic acid (2,4,5T), 2,4,5-trichlorophenol, pentachlorophenol and 3-chlorobenzoic acid, in both the culture medium and after incubation of cell free extracts with the chlorinated compounds. Electrophoresis of cell-free extracts in native polyacrylamide gel and staining for Cl− after incubation with 2,4-D and 2,4,5-T show multiple bands of enzyme activities which are unique for the isolate and also distinct from those of *Alcaligenes eutrophus*, which is also known to contain enzymes for the degradation of the aromatic chloro-compounds. The enzymes expressed by NRRL B-18086 can be used to detoxify a large group of chlorinated organics.

Pseudomonas NRRL B-18086 was grown and maintained in a Basal Salt Medium with 2,4-D, although other media conditions can be used. The composition of the medium used for one liter of water is given below:

| 2, 4 D | · | 1.7 gm |
|---|---|---|
| $K_2HPO_4$ | · | 5.8 gm |
| $KH_2PO_4$ | · | 4.5 gm |
| $(NH_4)_2SO_4$ | · | 2.0 gm |
| $MgCl_2$ | → | 0.16 gm |
| $CaCl_2$ | → | 20.0 mg |
| $NaMoO_4$ | → | 2.0 mg |
| $MnCl_2$ | → | 1.0 mg |
| | In One (1) Liter | |

What is claimed is:

1. A biologically pure culture of the microorganism Pseudomonas strain NRRL B-18086 and mutations thereof.

2. A process for degrading chloroaromatic waste comprising the steps of adding a biologically pure culture of Pseudomonas having the identifying characteristics of NRRL B-18086 to said waste.

3. A process according to claim 2 wherein said waste comprises 2,4-dichlorophenoxyacetic acid (2,4 D) and 2,4,5-trichlorophenoxyacetic acid (2,4,5-T).

* * * * *